(12) United States Patent
Roux et al.

(10) Patent No.: US 8,007,770 B1
(45) Date of Patent: Aug. 30, 2011

(54) PURIFIED LINEAR POLYPEPTIDE EPITOPES FROM WALNUTS AND ASSOCIATED METHODS

(75) Inventors: Kenneth H. Roux, Tallahassee, FL (US); Shridhar K. Sathe, Tallahassee, FL (US); Jason M. Robotham, Tallahassee, FL (US); Suzanne S. Teuber, Davis, CA (US)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 0 days.

(21) Appl. No.: 12/842,575

(22) Filed: Jul. 23, 2010

Related U.S. Application Data

(62) Division of application No. 11/829,120, filed on Jul. 27, 2007, now Pat. No. 7,763,721, and a division of application No. 10/251,918, filed on Sep. 20, 2002, now Pat. No. 7,250,489.

(60) Provisional application No. 60/324,161, filed on Sep. 20, 2001.

(51) Int. Cl.
*A61K 49/00* (2006.01)
*A61K 39/00* (2006.01)
*A61K 39/35* (2006.01)
*A61K 38/10* (2006.01)
*A61B 8/00* (2006.01)
*G01N 33/53* (2006.01)
*C07K 7/08* (2006.01)

(52) U.S. Cl. ............... 424/9.2; 424/9.81; 424/184.1; 424/185.1; 424/275.1; 435/4; 435/7.1; 530/300; 530/327

(58) Field of Classification Search .................. None
See application file for complete search history.

(56) References Cited

OTHER PUBLICATIONS

Teuber et al. Journal Allergy Clinical Immunology. 1998. 101: 807-814.*

* cited by examiner

*Primary Examiner* — Carla Myers
(74) *Attorney, Agent, or Firm* — Allen, Dyer, Doppelt, Milbrath & Gilchrist

(57) ABSTRACT

A purified Ig-E binding immunogenic polypeptide the amino acid sequence of which consists of SEQ ID NO:1 is disclosed. The purified amino acid sequence is a major allergen of the walnut *Juglans regia*. Also described are a diagnostic test kit and use of the purified polypeptide in tests for identifying patients having an allergy to walnuts. Mutations of the disclosed polypeptide, as well as nucleic acid sequences encoding therefor are claimed as part of the invention.

3 Claims, 7 Drawing Sheets

A

SEQ ID NO:4

QHFRQCCQQLSQMDEQCQCEGLRQVVRRQQQQQGLRGEEMEEMVQSARDLPNECGISSQRCEIRGGG

1 — 64

(brackets labeled 1 through 19 spanning the sequence)

B

SEQ ID NO:5

PRRGEGCREQIQRQQNLNHCQYYLRGG

1 — 26

(brackets labeled 20 through 25 spanning the sequence)

fig. 1.

Patient sera number 4  32  35  38  42  68  78  98  100  115  139 rJug r 1 –

152  160  172  173  178  191  218  223  237  C1  C2  2Ab rJug r 1 – fig. 2.

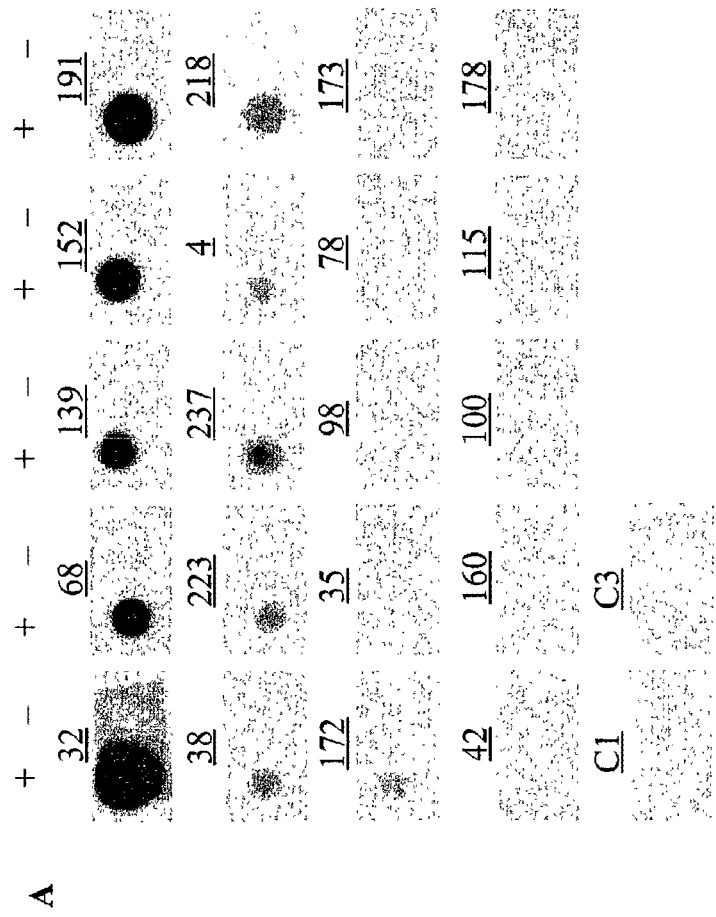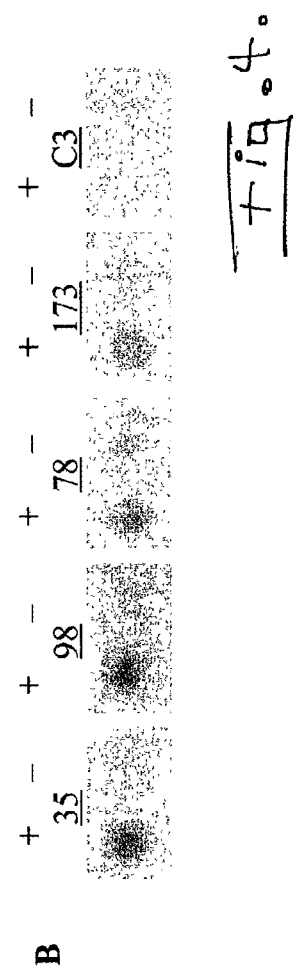
Fig. 4

Mutational analysis of the Jug r 1 IgE binding epitope, E1

| Amino Acid Sequence* | Substitution | IgE binding** |
|---|---|---|
| AGLRGEEMEEMV | Q1A | ++ |
| QALRGEEMEEMV | G2A | ++ |
| QGARGEEMEEMV | L3A | + |
| QGLAGEEMEEMV | R4A | − |
| QGLRAEEMEEMV | G5A | − |
| QGLRGAEMEEMV | E6A | − |
| QGLRGEAMEEMV | E7A | − |
| QGLRGEEAEMV | M8A | ++ |
| QGLRGEEMAEMV | E9A | ++ |
| QGLRGEEMEAMV | E10A | + |
| QGLRGEEMEEAV | M11A | ++ |
| QGLRGEEMEEMA | V12A | ++ |
| QAARGEEMEEMV | G2A, L3A | + |
| QAAAGEEMEEMV | G2A, L3A, R4A | − |
| QAAAAEEMEEMV | G2A, L3A, R4A, G5A | − |
| QGLRGEEMEAAV | E10A, M11A | + |
| QGLRGEEMAAAV | E9A, E10A, M11A | − |
| QGLRGEEAAAAV | M8A, E9A, E10A, M11A | − |

* The core amino acid residues, located at positions 36-39 of the large subunit, and an influential glutamic acid residue at position 42, are indicated in bold type. Mutated residues are underlined. *SEQ ID NO:1

** Peptides were probed with pooled with pool 1, comprised of sera from six walnut-sensitive patients.

Fig. 7.

AMINO ACID SEQUENCE* FOR IMMUNOGENIC WALNUT POLYPEPTIDE AND CORRESPONDING CODONS

| | | | |
|---|---|---|---|
| Q | Gln | Glutamine | CAA, CAG |
| G | Gly | Glycine | GGA, GGG. GGU, GGC |
| L | Leu | Leucine | UUA, UUG, CUU, CUC, CUA, CUG |
| R | Arg | Arginine | CGU, CGC, CGA, CGG, AGA, AGG |
| G | Gly | Glycine | GGA, GGG. GGU, GGC |
| E | Glu | Glutamic acid | GAA, GAG |
| E | Glu | Glutamic acid | GAA, GAG |
| M | Met | Methionine | AUG |
| E | Glu | Glutamic acid | GAA, GAG |
| E | Glu | Glutamic acid | GAA, GAG |
| M | Met | Methionine | AUG |
| V | Val | Valine | GUU, GUC, GUA, GUG |

*SEQ ID NO: 1

SEQUENCE LISTING

```
<160> NUMBER OF SEQ ID NOS: 10

<210> SEQ ID NO 1
<211> LENGTH: 12
<212> TYPE: PRT
<213> ORGANISM: Juglans regia

<400> SEQUENCE: 1

Gln Gly Leu Arg Gly Glu Glu Met Glu Glu Met Val
1               5                   10

<210> SEQ ID NO 2
<211> LENGTH: 4
```

<212> TYPE: PRT
<213> ORGANISM: Juglans regia

<400> SEQUENCE: 2

Arg Gly Glu Glu
1

<210> SEQ ID NO 3
<211> LENGTH: 7
<212> TYPE: PRT
<213> ORGANISM: Juglans regia

<400> SEQUENCE: 3

Gly Leu Arg Gly Glu Glu Met
1               5

<210> SEQ ID NO 4
<211> LENGTH: 64
<212> TYPE: PRT
<213> ORGANISM: Juglans regia

<400> SEQUENCE: 4

Gln His Phe Arg Gln Cys Cys Gln Gln Leu Ser Gln Met Asp Glu Gln
1               5                   10                  15

Cys Gln Cys Glu Gly Leu Arg Gln Val Val Arg Arg Gln Gln Gln Gln
                20                  25                  30

Gln Gly Leu Arg Gly Glu Glu Met Glu Glu Met Val Gln Ser Ala Arg
            35                  40                  45

Asp Leu Pro Asn Glu Cys Gly Ile Ser Ser Gln Arg Cys Glu Ile Arg
    50                  55                  60

<210> SEQ ID NO 5
<211> LENGTH: 26
<212> TYPE: PRT
<213> ORGANISM: Juglans regia

<400> SEQUENCE: 5

Pro Arg Arg Arg Gly Glu Gly Cys Arg Glu Gln Ile Gln Arg Gln Gln
1               5                   10                  15

Asn Leu Asn His Cys Gln Tyr Tyr Leu Arg
                20                  25

<210> SEQ ID NO 6
<211> LENGTH: 11
<212> TYPE: PRT
<213> ORGANISM: Juglans regia

<400> SEQUENCE: 6

Leu Ser Gln Arg Gly Leu Gln Ser Ser Ser Val
1               5                   10

<210> SEQ ID NO 7
<211> LENGTH: 7
<212> TYPE: PRT
<213> ORGANISM: Juglans regia

<400> SEQUENCE: 7

Gly Leu Arg Gly Glu Glu Met
1               5

<210> SEQ ID NO 8
<211> LENGTH: 11
<212> TYPE: PRT
<213> ORGANISM: Juglans regia

```
-continued

<400> SEQUENCE: 8

Leu Ser Gln Arg Ser Gln Gln Gln Cys Arg Gln
1               5                   10

<210> SEQ ID NO 9
<211> LENGTH: 13
<212> TYPE: PRT
<213> ORGANISM: Juglans regia

<400> SEQUENCE: 9

Gln Gln Gln Gly Leu Arg Gly Glu Glu Met Glu Glu Met
1               5                   10

<210> SEQ ID NO 10
<211> LENGTH: 13
<212> TYPE: PRT
<213> ORGANISM: Juglans regia

<400> SEQUENCE: 10

Gly Leu Arg Gly Glu Glu Met Glu Glu Met Val Gln Ser
1               5                   10
```

PURIFIED LINEAR POLYPEPTIDE EPITOPES FROM WALNUTS AND ASSOCIATED METHODS

RELATED APPLICATION

This application claims priority from and is a division of application Ser. No. 11/829,120 filed on Jul. 27, 2007, now U.S. Pat. No. 7,763,721, which was a division of Ser. No. 10/251,918, filed on Sep. 20, 2002, now U.S. Pat. No. 7,250,489, and which claimed priority from provisional application Ser. No. 60/324,161, filed on Sep. 20, 2001, all of which are incorporated herein by reference in their entirety.

FIELD OF THE INVENTION

The present invention relates to the field of allergies to nuts and, more particularly, to a purified linear epitope polypeptide from walnuts and associated methods.

SEQUENCE LISTING

A Sequence Listing is submitted herewith as an ASCII compliant text file throughout the Electronic Filing System; the name of the text file is "Purified Linear Polypeptide Epitope from Walnuts": the file was created on Aug. 4, 2006 and is 3 kilobytes in size: this Sequence Listing is incorporated herein by reference in its entirety.

BACKGROUND OF THE INVENTION

It is estimated that up to 8% of children less than 3 years of age and 2% of adults are affected by food allergies (reviewed in [1]). While food-induced allergic reactions are the most common cause of outpatient anaphylaxis,[2] the majority of severe reactions of this kind are caused by peanuts and tree nuts.[3,4] Most plant food allergens can be found among pathogenesis-related proteins, seed storage albumins and globulins, and a-amylase and protease inhibitors.

A previous study by Teuber et al.[6] documented the cloning and sequencing of a gene encoding Jug r 1, a major allergen in the English walnut, *Juglans regia*. Jug r 1 is a 2S albumin seed storage protein and possesses important homologies in amino acid sequence with other 2S albumin proteins from Brazil nut, cottonseed, castor bean, and mustard.6 Like many 2S albumins, Jug r 1 is synthesized as a precursor protein and cleaved into a large and small subunit joined by disulfide bridges. It is currently believed that patients with life-threatening allergies to walnuts and other tree nuts will rarely become tolerant of these foods[7] and consequently face a lifetime of avoidance.[8] Avoidance, however, is often difficult due to the ubiquitous nature of these foods and the potential for cross-contamination during their processing.[7]

Many approaches to allergen immunotherapy under investigation today are based on a detailed knowledge of the amino acids found in IgE-reactive B-cell epitopes.[9,10,11,12] These reactive sites can be either linear or conformational. Typically, a linear epitope contains a stretch of contiguous amino acids spanning 5-10 residues in the antigen, while residues distant in the primary sequence but proximate in the folded protein comprise a conformational epitope.[13] In recent years, the genes encoding several proteins with allergenicity, such as Jug r 1, have been cloned and expressed using molecular biology techniques.[6,14,15,16] Despite the rapidly increasing number of recombinant allergens, relatively few IgE-reactive B-cell epitopes have been defined.[17-29]

REFERENCES CITED

1. Sampson H A. Food allergy. Part 1: Immunopathogenesis and clinical disorders. J Allergy Clin Immunol 1999; 103: 717-28. Review.
2. Yocum M W, Khan D A. Assessment of patients who have experienced anaphylaxis: a 3-year survey. Mayo Clin Proc 1994; 69:16-23.
3. Sampson H A, Mendelson L M, Rosen J P. Fatal and near-fatal anaphylactic reactions to food in children and adolescents. N Engl J Med 1992; 327:380-4.
4. Yunginger J W, Sweeney K G, Sturner W Q, Giannanadra L A, Teigland J D, Bray M, et al. Fatal food-induced anaphylaxis. JAMA 1988; 260:1450-2.
5. Breiteneder H, Ebner C. Molecular and biochemical classification of plant-derived food allergens. J Allergy Clin Immunol 2000; 106:27-36.
6. Teuber S S, Dandekar A M, Peterson W R, Sellers C L. Cloning and sequencing of a gene encoding a 2S albumin seed storage protein precursor from English walnut (Juglans regia), a major food allergen. J Allergy Clin Immunol 1998; 101:807-14.
7. Bock S A, Atkins F M. The natural history of peanut allergy. J Allergy Clin Immunol 1989; 83:900-4.
8. Sicherer S H, Munoz-Furlong A, Burks W A, Sampson H A. Prevalence of peanut and tree nut allergy in the US determined by a random digit dial telephone survey. J Allergy Clin Immunol 1999; 103:559-562.
9. Valenta R, Vrtala S, Focke-Tejkl M, Bugajska-Schretter A, Ball T, Twardosz A, et al. Genetically engineered and synthetic allergen derivatives: Candidates for vaccination against Type I allergy. Biol. Chem. 1999; 380:815-24.
10. van Neerven R J J. The role of allergen-specific T cells in the allergic immune response: relevance to allergy vaccination. Allergy 1999; 54:552-61.
11. Bindslev-Jensen C, Poulsen L K. In vitro diagnostic methods in the evaluation of food hypersensitivity. In: Food Allergy: Adverse Reactions to Foods and Food Additives, 1997, Blackwell Science; 137-50.
12. Vrtala S, Ball T, Spitzauer S, Pandjaitan B, Suphioglu C, Knox B, et al. Immunization with purified natural and recombinant allergens induces mouse IgG1 antibodies that recognize similar epitopes as human IgE and inhibit the human IgE-allergen interaction and allergen-induced basophil degranulation. J. Immunol. 1998; 160:6137-44.
13. Zhao Y, Chait B T. Protein epitope mapping by mass spectrometry. Anal Chem 1994; 66:3723-6.
14. Dolecek C, Vrtala S, Laeffer P, Steinberger P, Kraft D, Sheiner O, Valenta R. Molecular characterization of Phl p 2, a major timothy grass (*phleum pratense*) pollen allergen. FEBS Lett 1993; 335:299-04.
15. Ghosh B, Perry M P, Marsh D G. Cloning the cDNA encoding the Amb t V allergen from giant ragweed (Ambrosia trifida). Gene 1991; 101:231-8.
16. Scheiner O, Kraft D. Basic and practical aspects of recombinant allergens. Allergy 1995; 50:384-91.
17. Elsayed S, Titlestad K, Apold J, Aas K. A synthetic hexadecapeptide derived from allergen M imposing allergenic and antigenic reactivity. Scand J Immunol 1980; 12:171-5.
18. Atassi H, Atassi M Z. Antibody recognition of ragweed allergen Ra3: localization of the full profile of the continuous antigenic sites by synthetic overlapping peptides representing the entire protein chain. Eur J Immunol 1986; 16:229-35.
19. Mazur G, Baur X, Modrow S, Becker W M. A common epitope on major allergens from non-biting midges (Chironomidae). Mol Immunol 1988; 25:1005-10.

20. van't H of W, van Milligen F J, van den Berg M, Lombardero M, Chapman M D, Aalberse R C. Epitope mapping of the cat (*Felis domesticus*) major allergen Fel d I by overlapping synthetic peptides and monoclonal antibodies against native and denatured Fel d I. Allergy. 1993; 48:255-63.
21. Helm R M, Cockrell G, Connaughton C, West C M, Herman E, Sampson H A, Bannon G A, Burks A W. Mutational analysis of the IgE-binding epitopes of P34/Gly m Bd 30K. J Allergy Clin Immunol 2000; 105:378-84.
22. Helm R, Cockrell G, Herman E, Burks A, Sampson H, Bannon G. Cellular and molecular characterization of a major soybean allergen. Int Arch Allergy Immunol 1998; 117:29-37.
23. Banerjee B, Greenberger P A, Fink J N, Kurup V P. Conformational and linear B-cell epitopes of Asp f 2, a major allergen of *Aspergillus fumigatus*, bind differently to immunoglobulin E antibody in the sera of allergic bronchopulmonary aspergillosis patients. Infect Immun 1999; 67:2284-91.
24. van't H of W, Driedijk P C, van den Berg M, Beck-Sickinger A G, Jung G, Aalberse R C. Epitope mapping of the Dermatophagoides pteronyssinus house dust mite major allergen Der p II using overlapping synthetic peptides. Mol Immunol 1991; 28:1225-32.
25. Walsh B J, Howden M E. A method for the detection of IgE binding sequences of allergens based on a modification of epitope mapping. J Immunol Methods 1989; 121:275-80.
26. Elsayed S, Nolen E, Dybendal T. Synthetic allergenic epitopes from the amino-terminal regions of the major allergens of hazel and birch pollen. Int Arch Allergy Appl Immunol 1989; 89:410-5.
27. Burks A W, Shin D, Cockrell G, Stanley J S, Helm R M, Bannon G A. Mapping and mutational analysis of the IgE-binding epitopes on Ara h 1, a legume vicilin protein and a major allergen in peanut hypersensitivity. Eur J Biochem 199715; 245:334-9.
28. Stanley J S, King N, Burks A W, Huang S K, Sampson H A, Cockrell G, Helm R M, West C M, Bannon G A. Identification and mutational analysis of the immunodominant IgE binding epitopes of the major peanut allergen Ara h 2. Arch Biochem Biophys 1997 15; 342:244-53.
29. Rabjohn P, Helm E M, Stanley J S, West C M, Sampson H A, Burks A W, Bannon G A. Molecular cloning and epitope analysis of the peanut allergen Ara h 3. J Clin Invest 1999; 103:535-42.
30. Frangioni J V, Neel B G. Solubilization and purification of enzymatically active glutathione S-transferase (pGEX) fusion proteins. Anal Biochem 1993; 210:179-87.
31. Sze-Tao K W C, Sathe S K. Walnuts (Juglans regia L): proximate composition, protein solubility, protein amino acid composition and protein in vitro digestibility. J Sci Food Agric 2000; 80:1393-01.
32. Foucard T, Malmheden Yman I. A study on severe food reactions in Sweden—is soy protein an underestimated cause of food anaphylaxis? Allergy 1999; 54:261-5.
33. Bock S A, Munoz-Furlong A, Sampson H A. Fatalities due to anaphylactic reactions to foods. J Allergy Clin Immunol 2001; 107:191-3.
34. Pastorello E A, Farioli L, Pravettoni V, Ispano M, Conti A, Ansaloni R, Rotondo F, Incorvaia C, Bengtsson A, Rivolta F, Trambaioli C, Previdi M, Ortolani C. Sensitization to the major allergen of Brazil nut is correlated with the clinical expression of allergy. J Allergy Clin Immunol 1998; 1021-7.
35. Bredehorst R, David K. What establishes a protein as an allergen? J Chrom B 2001; 756:33-40. Review.
36. Berzofsky J A. Intrinsic and extrinsic factors in protein antigenic structure. Science 1985; 229:932-40.
37. Smith L J, Munoz-Furlong A. The management of food allergy in: Food Allergy: Adverse Reactions to Foods and Food Additives, 1997, Blackwell Science; 431-44.
38. Sicherer S H, Sampson H A. Peanut and tree nut allergy. Curr Opin Pediatr 2000; 12:567-73.

SUMMARY OF THE INVENTION

With the foregoing in mind, the present invention advantageously provides a purified Ig-E binding immunogenic polypeptide comprising a walnut IgE-binding epitope. Peanut and tree nut allergies can be life threatening, and appear to be growing in prevalence. Jug r 1, a 2S albumin seed storage protein, was previously characterized as a major English walnut food allergen. Accordingly, we sought to identify the linear immunoglobulin E (IgE)-binding epitopes of Jug r 1 and determine which, if any, amino acids are necessary for this binding to occur. The aim of the research leading to the present invention was to screen the large and small subunits of the English walnut allergen Jug r 1, in search for linear IgE-binding epitopes. We have discovered a single immunodominant IgE-binding epitope, residing in the large subunit, and have identified the core amino acids necessary for this binding to occur.

Pools of sera from walnut-allergic patients and overlapping peptides synthesized on an activated cellulose membrane were used to screen for IgE-binding epitopes. Mutational analysis of the immunodominant epitope was carried out via single and multi-site amino acid substitutions. Inhibition assays were performed using affinity-purified IgE, soluble forms of the epitope peptide, and the recombinant 2S albumin, rJug r 1.

One immunodominant-linear epitope having twelve amino acid residues was identified, and is set forth herein as SEQ ID NO:1. Amino-acid mutations to the epitope demonstrated that the residues RGEE, at positions 4 to 7, were required for IgE binding. Probing of this epitope with each of 20 patients' sera revealed 15 were positive. Binding of patients' IgE to the epitope was inhibited with a soluble form of the peptide, however soluble peptide did not completely inhibit the binding of IgE to the intact rJug r 1.

One major linear IgE-reactive epitope and its required core amino acid residues have been identified. Mutation of any of these core amino acids resulted in loss of IgE binding to the epitope and therefore suggests the feasibility of reducing allergenicity in genetically modified walnuts by engineering nuts with a modified epitope sequence. Although this approach may be feasible, nevertheless, strong evidence for the existence of conformational epitopes was also obtained, thus, a fully non-allergenic bioengineered nut may require additional modifications.

BRIEF DESCRIPTION OF THE DRAWINGS

Some of the features, advantages, and benefits of the present invention having been stated, others will become apparent as the description proceeds when taken in conjunction with the accompanying drawings in which:

FIG. 1 shows the entire 64-amino acid length of the large subunit (FIG. 1A; SEQ ID NO:4) and 26-amino acid length of the small subunit (FIG. 1B; SEQ ID NO:5);

FIG. 2 dot-blot assay showing IgE from 20 individual walnut-sensitive patients binding to the 20-kDa His-tagged rJug r 1;

FIG. 4 results of the 20 patients tested, five exhibiting strong recognition of the epitope peptide, six moderate, four weak, and five showing no recognition; none reacted with the (−) peptide;

FIG. 5 shows binding of IgE to the positive (E1) peptide in unfractionated patient serum, progressively less binding in the first two eluate fractions, and no binding in the third, indicating complete removal of the E1-reactive Ab by the column (FIG. 5A); E1-adsorbed serum (effluent) showing no reactivity to the E1 peptide, confirms removal of E1-specific IgE from the serum; eluate and effluent fractions were then used in dot-blot assays to determine if IgE Abs to the E1 epitope represent the bulk of the rJug r 1-reactive IgE, with results showing binding of IgE to rJug r 1, from total sera and the first two eluate (anti-E1) fractions, but not the third (anti-E1-depleted) (FIG. 5B);

FIG. 6 is a table showing results of mutational analysis of the Jug r 1 IgE binding epitope designated E1, also referred to as SEQ ID NO:1; and FIG. 7 displays in tabular form the amino acid sequence for the present immunogenic walnut polypeptide (SEQ ID NO:1) and its corresponding codons.

DETAILED DESCRIPTION OF THE PREFERRED EMBODIMENT

Figure 3:
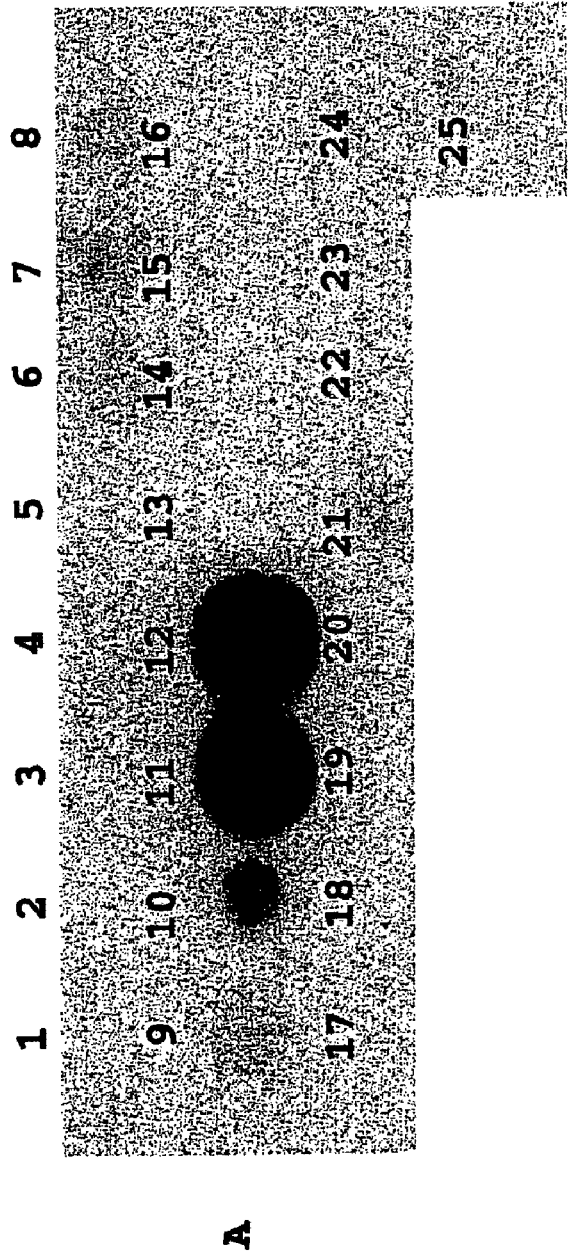
FIG. 3 shows results of a study of the entire lengths of both the large and small subunits of Jug r 1 carried out by probing overlapping solid phase synthetic peptides with sera from 20 patients randomly assigned to four pools; each pool recognized three adjacent peptides from the large subunit; two peptides were recognized very strongly (#'s 11 and 12) and one less so (#10); no peptides were identified from the small subunit (FIG. 3A); a common sequence, GLRGEEM, was observed in all three large subunit peptides (FIG. 3B; SEQ ID NO:3)

The present invention will now be described more fully hereinafter with reference to the accompanying drawings, in which preferred embodiments of the invention are shown. Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below.

All publications, patent applications, patents, and other references mentioned herein are incorporated by reference in their entirety. In case of conflict, the present specification, including any definitions, will control. In addition, the materials, methods and examples given are illustrative in nature only and not intended to be limiting. Amino acids are referred to by their standard single or three letter abbreviation. Similarly, nucleic acids are identified by their single letter code, as known in the art.

Accordingly, this invention may, however, be embodied in many different forms and should not be construed as limited to the illustrated embodiments set forth herein. Rather, these illustrated embodiments are provided so that this disclosure will be thorough and complete, and will fully convey the scope of the invention to those skilled in the art. Other features and advantages of the invention will be apparent from the following detailed description, and from the claims.

LIST OF ACRONYMS AND ABBREVIATIONS USED

ECL: enhanced chemiluminescence;
IgE: immunoglobulin E;
NC: nitrocellulose;
RT: room temperature;
ddH20: distilled-deionized water;
BSB: buffered saline borate;
TBS: tris-buffered saline;
TBS-T: tris-buffered saline with 0.2% Tween-20;
PBS: phosphate buffered saline;
GST: glutathione-S-transferase;
DMF: N,N-dimethylformamide;
Fmoc: 9-fluorenlymethoxy carbonyl-derived;
SDS-PAGE: sodium dodecylsulfate-polyacrylamide gel electrophoresis; and
Overnight: o/n.

Methods

Human Sera

The study was approved by the Human Subjects Review Committee at the University of California, Davis. Sera from 20 walnut-allergic patients with a convincing history of life-threatening systemic allergic reactions to walnuts, positive ImmunoCAP assays (Pharmacia, Inc., Diagnostics, Columbus, Ohio), and evidence of IgE against rJug r 1 (see below) were used in this study. Control sera were obtained from atopic patients with no history of walnut sensitivity, and one patient with life-threatening reactions to walnuts, positive ImmunoCAP assay, positive serum IgE immunoblot to walnut proteins, but negative for binding to the 2S albumin.

Expression and Isolation of rJug r 1

Two protocols for isolation of rJug r 1 were used. In the first, used to produce rJug r 1 for screening patient sera by Western blotting, the Jug r 1 insert was subcloned into the pPROEXHT expression vector (Gibco BRL, Invitrogen Life Technologies, Carlsbad, Calif.), and transformed into E. coli BL21-Codon Plus (Stratagene Inc., La Jolla, Calif.). Cells were grown overnight (o/n) at 37° C. in 5 ml 2×YT broth with 50 µg/ml ampicillin and chloramphenicol. This was then added to 500 ml 2×YT broth and grown to an $A_{600}$ of 1.0. Isopropyl thiogalactose was added to 0.5 mM, and the culture was grown at 37° C. for 4 hrs. Cells were pelleted, washed with 0.02 M phosphate buffered saline (PBS; pH 7.3), and resuspended in BRL Lysis Buffer (Gibco BRL). Lysozyme was added to 500 µg/ml on ice for 15 min, followed by the addition of sarkosyl to 1% w/v. The cells were sonicated and the insoluble matter pelleted by centrifugation at 12,000 g for 20 min at 4° C. Ni-NTA resin (Gibco BRL) was added in BRL Buffer A (Gibco BRL) to the supernatant and allowed to incubate o/n at 4° C. The resin was washed 4× with BRL Buffer A and the His-tagged fusion protein then eluted with BRL Buffer C (Gibco BRL) containing 0.25% sarkosyl. In the second protocol, rJug r 1 was expressed in fusion with glutathione-S-transferase (GST) and purified following the Frangioni and Neel protocol with slight modifications as previously described by Teuber et al [6, 30]. This GST-rJug r 1 fusion protein was used in all dot-blot assays, as described below.

Immunoblotting of rJug r 1 rJug r 1 samples were either subjected to sodium dodecylsulfate-polyacrylamide gel electrophoresis (SDS-PAGE) and electrophoretically transferred to nitrocellulose (NC), or blotted directly onto the membrane. For SDS-PAGE analysis of rJug r 1, samples were boiled for five min in sample buffer (60 mM Tris-HCl, pH 6.8, 2% SDS, 10% (v/v) glycerol, 0.01% (w/v) bromophenol blue) and electrophoresis was carried out at 8 mA constant current using a SE600 Vertical Slab Gel Unit (Pharmacia Biotech, Piscataway, N.J.). An SDS-PAGE gel, 13% monomer acrylamide concentration, with 1 µg protein/4 mm was used for immunoblotting as previously described.[6] Protein was transferred to a 0.22 mm NC membrane (MSI, Westborough, Mass.) o/n at 30V using a TE 42 Transphor Electro-Transfer Unit (Pharmacia Biotech, Piscataway, N.J.). The blot was cut into 4 mm wide strips and blocked for 1 hr at room temperature (RT) in PBS/3% nonfat dry milk/0.2% Triton X-100 (TX-100). Diluted sera, 1:5 v:v in the blocking buffer, were added to the strips and incubated o/n at RT. The strips were then washed for 20 min 3× in PBS/0.01% TX-100 and incubated o/n at RT with equine polyclonal $^{125}$I-anti-human IgE (Hycor Biomedical Inc., Garden Grove, Calif.) diluted 1:5 in the nonfat milk buffer. The strips were washed for 20 min 3× and exposed to Kodak Biomax x-ray film (Kodak, Rochester, N.Y.) at −70° C. for 48 hours. All incubations were carried out with rocking.

For dot-blot assays, a graphite pencil was used to circumscribe 4 mm×8 mm elipses on a dry 0.4 µm NC membrane (Shleicher & Schuell, Keen, N.H.). The NC was incubated in distilled-deionized water (ddH$_2$O) on a rocking table for 5 min and allowed to air dry before each dot was loaded with 0.11 µg of rJug r 1 in 2 µl of ddH$_2$O. The antigen-loaded NC was then rinsed in ddH$_2$O as described above, placed protein side up on 3 MM paper (Whatman Intl. Ltd., Maidstone, England), and dried under a 60-watt light until all moisture was removed. Once dry, dots were rinsed for 2 min in Tris-buffered saline (TBS: 20 mM Tris, 137 mM NaCl, pH 7.6) containing 0.2% Tween-20, blocked for 1 hr at RT in TBS-T containing 2% bovine-serum albumin (BSA, Sigma, St. Louis, Mo.), and then incubated o/n at 4° C. with sera diluted 1:40 in TBS-T. Membranes were then washed once for 15 min, and 3× for 5 min in TBS-T prior to being incubated for 1 hr at RT with horseradish peroxidase-labeled goat-anti-human IgE (Biosource International, Camarillo, Calif.) diluted 1:2000 in TBS-T. Washing in TBS-T was repeated as above and the reactive dots were identified after a 5-min incubation in Enhanced Chemiluminescence Plus (ECL+, Amersham Pharmacia, Piscataway, N.J.), prepared following manufacturer's instructions, and subsequent exposure to Kodak X-OMAT x-ray film.

Solid-Phase Peptide (SPOTs) Synthesis

Based on the published amino acid sequence of Jug r 1 and our unpublished data determining the subunit cleavage sites,[6] twenty-five 13-amino acid peptides, offset by three amino acids, were synthesized which corresponded to the entire 64-amino acid length of the large subunit (FIG. 1A) and 26-amino acid length of the small subunit (FIG. 1B). Additional peptides bearing the target epitope (QGLRGEEMEEMV), SEQ ID NO:1, mutated forms of this peptide, and a non-IgE binding peptide (LSQRGLQSSSV), SEQ ID NO:6, were also synthesized. Thirteen versions of the target peptide were created via a single site alanine substitution at each position along the amino acid sequence, and six mutated peptides were synthesized using multiple alanine substitutions, as shown in FIG. 6.

Peptides were synthesized on derivatized cellulose sheets using 9-fluorenlymethoxy carbonyl-derived (Fmoc) amino acids as described by the manufacturer (Genosys Biotechnologies, Inc., The Woodlands, Tex.). Briefly, cellulose membranes containing free hydroxy groups were esterfied with an Fmoc-amino acid dissolved in 1-methyl-2 pyrrolidinone. The coupling reaction was followed by washing in N,N-dimethylformamide (DMF) and the amino acids were acetylated with acetic anhydride. The membranes were deprotected by washing in DMF and incubation with a solution of 20% piperidine in DMF followed by another wash in DMF. Coupling, acetylation, and deprotection steps were repeated for each cycle. During the final cycle, a mixture of dichloromethane, trifluoroacetic acid, and triisobutylsilane (1:1:0.05) was used to deprotect the acid-labile amino acid side chains.

IgE Binding to Solid Phase Synthetic Peptides (SPOTs Analysis)

The peptide-containing membranes were washed in TBS and incubated o/n at RT in blocking solution as directed by the manufacturer (Genosys Biotechnologies, Inc., The Woodlands, Tex.). Membranes were then washed in TBS-T for 10 min and incubated o/n at 4° C. with individual patient's serum or pooled patients' sera diluted 1:5 in blocking buffer (total sera:blocking buffer). This incubation was followed by three 5-min washes in TBS-T and an o/n (4° C.) incubation with $^{125}$I-anti-human IgE (Hycor Biomedical Inc., Garden Grove, Calif.) diluted 1:10 in a mixture of PBS, 5% nonfat dry milk, and 0.05% Tween-20. Three final 10 min washes in PBS/0.05% Tween-20 were performed and IgE-peptide reactivity identified after a 48 hr exposure at −70° C. to Kodak Biomax x-ray film.

Soluble Epitope Peptide Synthesis

A soluble form of an identified IgE-reactive peptide (QGLRGEEMEEMV; SEQ ID NO: 1) was synthesized by Fmoc protocols on an automated peptide synthesizer (Model 433A, Applied Biosystems, Foster City, Calif.).

Isolation and Inhibition of Epitope-Specific IgE

The epitope-reactive IgE was isolated from patients' sera by affinity chromatography. A 0.5 ml pool of patients' sera, known to be reactive to the reactive synthetic solid-phase epitope peptide, was slowly added to a 5 ml disposable polypropylene column (Pierce Chemical Company, Rockford, Ill.) containing cyanogen-bromide-activated beads (Sigma, St. Louis, Mo.) (to which 5 mg of the reactive peptide had been covalently coupled, as described by the manufacturer) and the effluent collected. Bound IgE was eluted with the addition of 0.2 M glycine sulfate, pH 2.3, collected in a beaker containing 10 µl of 1% BSA in buffered saline borate (BSB), and subsequently neutralized with 1.0 M Tris. The column was then rinsed with BSB and the initial effluent re-passed over the column. The process was repeated for a total of 3×, yielding three eluates and the column effluent.

To test the specificity and reactivity of the epitope-specific IgE, control, pooled and fractionated patients' sera were pre-incubated o/n at 4° C. with different amounts (70, 7.0, and 0.7 µg) of the soluble epitope peptide, or a soluble non-specific peptide. The pre-incubated sera were used to probe either solid phase IgE-reactive and non-IgE-reactive peptides or rJug r 1. Detection of IgE binding to the solid-phase synthetic peptides and dot-blotted rJug r 1 was detected using $^{125}$I-anti-human IgE and ECL+, respectively, as described earlier.

IgE Binding to rJug r 1

IgE from 20 individual walnut-sensitive patients was shown to bind the 20-kDa His-tagged rJug r 1 (FIG. 2). Three showed only faint binding, while 17 sera gave moderate or strong signals. Recombinant Jug r 1 was previously shown to completely inhibit binding to the native 2S albumin and substantially inhibit binding of patient sera IgE to English walnut in walnut ImmunoCAP assays (up to 84% of measurable anti-walnut IgE),[6] thus the folding appears to preserve most of the presumed conformational epitopes present on the native mature protein.

Identification and Recognition of IgE-Reactive Linear Epitopes on rJug r 1

The entire lengths of both the large and small subunits of Jug r 1 were studied by probing overlapping solid phase synthetic peptides with sera from 20 patients randomly assigned to four pools. Each pool recognized three adjacent peptides from the large subunit; two peptides were recognized very strongly (#s 11 and 12) and one less so (#10); no peptides were identified from the small subunit (FIG. 3A). A common sequence, GLRGEEM (SEQ ID NO:7), was observed in all three large subunit peptides (FIG. 3B). A fourth partially overlapping sequence (#9, FIG. 3A) showed a slight positive reaction. Some other peptides showed slight positive signals in some assays (i.e. #7, FIG. 3A) but were not reproducible, leading us to examine only the identified dominant linear epitope-bearing peptides. Additional peptides were tested in which alanine was substituted at each of the 12 amino residues of the IgE-reactive peptide, QGLRGEEMEEMV (SEQ ID NO: 1). In addition, peptides were tested with varying numbers of alanines substituted at the N- and C-termini. Together, these data demonstrated that the core amino acids RGEE, at positions 36 to 39, and an additional glutamic acid residue at position 42, were necessary for maximum IgE binding to occur (FIG. 6). SPOTs containing a 12-amino acid peptide (QGLRGEEMEEMV; SEQ ID NO: 1), bearing the immunodominant epitope, designated E1, and SPOTs containing a negative control (−) peptide (LSQRSQQQCRQ; SEQ ID NO:8), selected from the large subunit of Jug r 1 were used to test the degree of individual reactivity and specificity of allergic and control sera.

Of the 20 patients tested, five exhibited strong recognition of the epitope peptide, six moderate, four weak, and five showed no recognition; none reacted with the (−) peptide (FIG. 4).

Isolation and Inhibition of E1-Specific IgE

Figure 5:
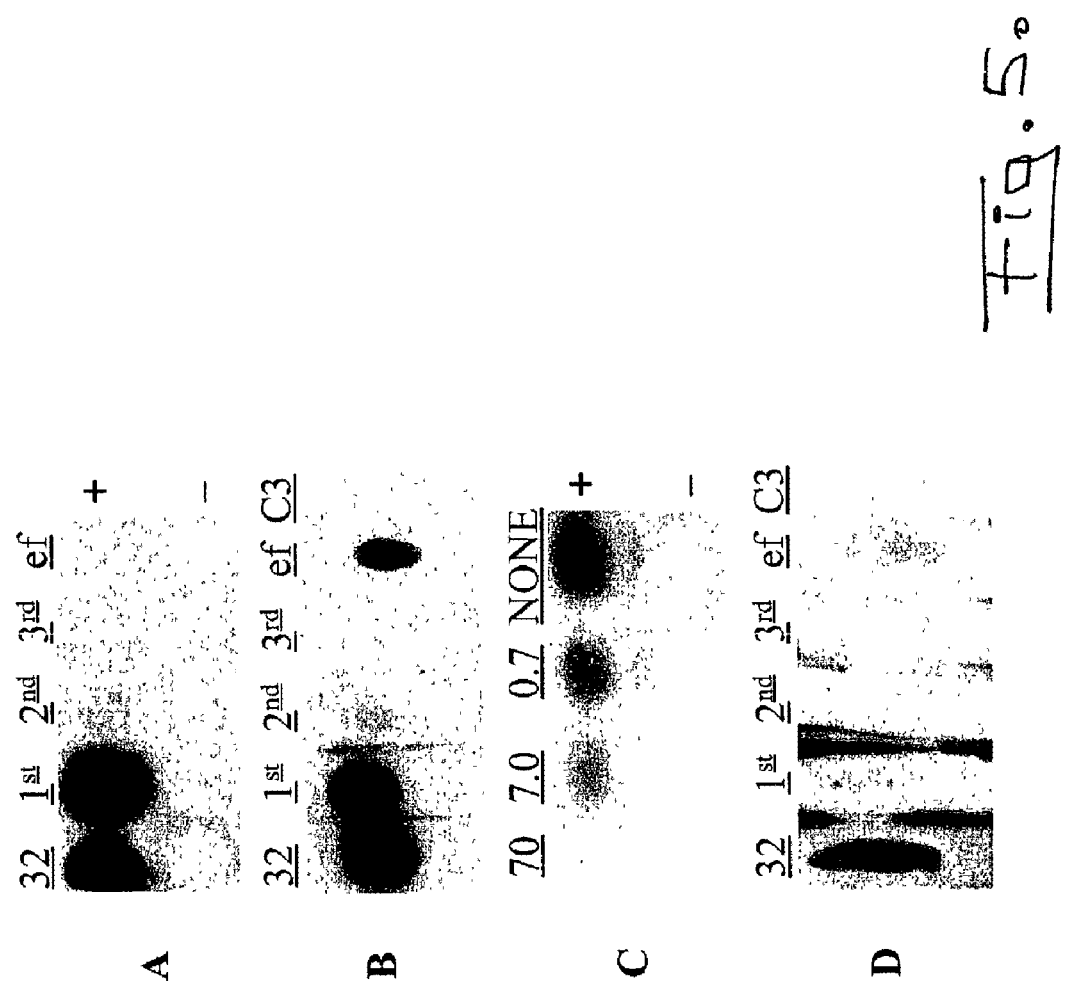

To determine if the identified epitope, designated E1, is the major epitope recognized by patients' sera, we separated E1-specific IgE from the total antiserum and tested both fractions for reactivity with rJugr 1. Epitope-specific IgE was isolated from patient serum by passage over an E1-affinity column. To assure removal of anti-E1 Abs, the three sequential eluate and the serum effluent fractions were first assayed against our solid-phase IgE binding (+) and non-IgE binding (−) peptides. FIG. 5A shows binding of IgE to the positive (E1) peptide in unfractionated patient serum, progressively less binding in the first two eluate fractions, and no binding in the third, indicating complete removal of the E1-reactive Ab by the column. Significantly, the E1-adsorbed serum (effluent) also showed no reactivity to the E1 peptide, confirming removal of E1-specific IgE from the serum. The eluate and effluent fractions were then used in dot-blot assays to determine if IgE Abs to the E1 epitope represent the bulk of the rJug r 1-reactive IgE. As expected, binding of IgE to rJug r 1, from total sera and the first two eluate (anti-E1) fractions, but not the third (anti-E1-depleted), was demonstrated (FIG. 5B). However, there was considerable rJug r 1-specific IgE remaining in the effluent (anti-E1 depleted fraction), demonstrating the presence of additional IgE Ab specific for one or more conformational epitopes.

To further examine the specificity of both our peptide-reactive fractions and unfractionated Jug r 1-reactive IgE, a soluble form of the epitope peptide was pre-incubated with whole patient serum as well as the E1-specific IgE Abs in an attempt to inhibit their reaction with both our solid-phase peptides and rJugr 1. Varying amounts (70, 7.0, 0.7 μg) of the peptide were incubated with whole patients' sera prior to probing the E1 epitope (positive) and negative solid-phase peptides. Partial to complete inhibition was achieved (FIG. 5C), demonstrating that the solid and fluid phase versions of the peptide are similarly recognized. The amount of soluble peptide (70 μg) needed to completely inhibit binding of E1-specific IgE to the solid phase version of this epitope was similarly used for inhibition studies involving unfractionated patient serum IgE and affinity column purified IgE fractions against the rJug r 1. Inhibition was again observed in the eluate (E1 epitope-specific) IgE fractions.

These data demonstrate that the epitope is similarly recognized in both the peptide and the recombinant protein. However, IgE reactivity in both whole patient serum and the E1-adsorbed effluent fraction reacted with rJug r 1 (FIG. 5D), again demonstrating the existence of additional (presumably conformational) IgE-reactive epitopes on rJug r 1.

DISCUSSION

On a global basis walnuts rank second in tree nut production.[31] In children, anaphylactic reactions to peanut and tree nuts are responsible for most fatal and near-fatal food allergic reactions.[3, 32] In a recent study, 32 fatal cases of anaphylactic reactions to foods reported to a national registry were analyzed and it was determined that up to 31% were due to tree nuts.[33] The severity and prevalence of some food induced allergic reactions has prompted investigation to identify and characterize offending allergens.

Jug r 1, a major allergen in the English walnut, has previously been characterized as a 2S albumin seed storage protein.[6] 2S albumins are found in almost all edible seeds. In view of the importance of this class of protein as food allergens and the possibility of cross-reactivity among class-related proteins,[34] a detailed knowledge of these proteins would be valuable. In particular, given the important role allergen-specific IgE plays in the allergic reaction, determination of allergen-specific IgE binding epitopes, be they linear or conformational, appears to be of great importance for gaining a better understanding of the allergenic nature of foods and for possible therapeutic intervention.

We have found a single linear IgE-reactive epitope and have defined its core amino acid residues. To date, no common structural character of linear-IgE epitopes has been identified (reviewed in[35]), but this could change as more epitope mapping studies are completed. A key step in the allergic reaction is the binding of at least two IgE Abs to a multivalent allergen. The fact that we have found only one linear epitope on Jug r 1 is unique in that all previously analyzed allergens have contained multiple linear IgE-binding sites (reviewed in[35]). Although we cannot rule out the existence of weakly binding peptides that are undetected by our methods, the affinity of such peptides would be much lower as judged by the high intensity of the signal on the epitope E1. Our findings, in combination with the knowledge that allergens must be multivalent to elicit an allergic response, point towards the existence of conformational epitopes on Jug r 1 as well. Although it is qualitative data, it is noteworthy that all 20 patients' sera bound rJug r 1 (in FIG. 2), whereas only 15 bound the linear epitope, with many of these exhibiting disproportionately faint binding. This too, is evidence that conformational epitopes are relevant and key in IgE binding for some patient sera. In fact, it has been estimated that most protein epitopes are conformational.[36] It is worthwhile to note that the labeling of an epitope as "linear", based on the use of synthetic epitopes, is imprecise because the identified epitope may be a fragmented part of a larger discontinuous epitope (reviewed in[35]).

Clinically, insight into the IgE-binding epitopes of allergens, linear or conformational, is extremely useful. Identifying the immunodominant linear IgE-binding epitope of Jug r 1 may lead to better designs for walnut-allergy therapy. Currently there is no generally agreed upon treatment for IgE-mediated food allergy and, therefore, complete avoidance of the food is recommended.[37] However, with tree nuts, such as walnuts, avoidance is often difficult since equipment used for food processing is often shared and the implicated allergen may, therefore, be present in trace amounts or may be added to foods where its presence was not expected by the consumer. Because tree nut allergies are rarely resolved, reactions can be severe, and accidental ingestion is almost inevitable, life for afflicted patients can be fraught with anxiety (reviewed in[38]). Some new approaches to allergen immunotherapy and diagnosis include: the use of blocking peptides to inhibit the triggering of IgE-mediated hypersensitivity reactions, immunization with specific peptides to alter the type of immune response elicited, allergen reengineering to enhance protective responses, and the use of defined peptides in diagnostic assays.[9,10,11,12] A common factor for the application of these approaches is a required knowledge of the amino acids in the IgE-reactive sites of the allergen. We have mapped the major linear IgE epitope of Jug r 1 and identified the principal core amino acid residues within the epitope. Additional studies are planned to identify the conformational epitopes on this allergen.

Accordingly, the invention disclosed herein includes a purified Ig-E binding immunogenic polypeptide of walnuts, the amino acid sequence of which consists of SEQ ID NO:1. The immunogenic polypeptide of the invention may also include at least one mutation in said amino acid sequence, wherein said at least one mutation is selected from a deletion, a substitution, and an addition. The polypeptide may also comprise at least one mutation in said amino acid sequence which reduces the polypeptide's IgE-binding capacity while maintaining at least minimal immunogenicity. The skilled will recognize that the inventive polypeptide may also comprise at least two SEQ ID NO:1.

The invention additionally includes a test for detecting a walnut allergy in a patient, said test comprising contacting the patient with an effective amount of a purified polypeptide consisting of SEQ ID NO:1 for detecting the allergy. In one embodiment of the test contacting comprises injecting the purified polypeptide below the skin of the patient. For use in this test, the purified polypeptide may comprise at least one mutation in said sequence, and the mutation is selected from a deletion, a substitution, and an addition.

A further embodiment of the invention includes a diagnostic test for detecting anti-walnut IgE in a patient to thereby indicate an allergy to walnuts. The diagnostic comprises reacting patient's serum with a purified polypeptide the amino acid sequence of which consists of at least one SEQ ID NO:1; separating the polypeptide from unreacted patient serum; reacting the polypeptide with a labeled human IgE-reactive agent after separating from unreacted patient serum; separating the polypeptide from unreacted labeled human IgE-reactive agent; and directly or indirectly detecting the labeled human IgE-reactive agent bound to the polypeptide after separating from unreacted agent to thereby indicate presence in the patient's serum of anti-walnut IgE. For use in this diagnostic test, as also noted previously, the amino acid sequence may further comprise at least one mutation selected from a deletion, a substitution, and an addition.

Yet another embodiment of the invention includes a test kit for screening patients for allergy to walnuts. The kit comprises a first reagent containing at least one purified polypeptide whose amino acid sequence consists of SEQ ID NO:1. The kit also contains a second reagent containing at least one labeled human IgE-reactive agent, for example, anti human IgE, or others known or to be developed. In the test kit, the first reagent preferably comprises a solid phase carrying the purified polypeptide.

Those skilled in the art will readily recognize that from a known amino acid sequence such as SEQ ID NO:1, we may readily prepare an isolated nucleic acid sequence and degenerate variants thereof which encode a polypeptide consisting of SEQ ID NO:1, as shown in FIG. 7. Such a nucleic acid may further comprise a sequence which encodes at least one mutation of SEQ ID NO:1, wherein said mutation is selected from a deletion, a substitution, and an addition. The nucleic acid may be an isolated cDNA and degenerate variants thereof which encode a polypeptide consisting of SEQ ID NO:1, or at least one mutation thereof wherein said mutation is selected from a deletion, a substitution, and an addition.

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

That which is claimed:

1. A test for detecting a walnut allergy in a patient, the test comprising:
   contacting the patient with an effective amount of a purified polypeptide consisting of SEQ ID NO: 1; and
   detecting whether said contacting the patient results in an allergic response, wherein an allergic response is indicative of a walnut allergy in the patient.

2. The test of claim 1, wherein contacting comprises contacting the skin of the patient.

3. The test of claim 1, wherein contacting comprises injecting the patient.

* * * * *